(12) United States Patent
Erdman

(10) Patent No.: US 6,610,161 B2
(45) Date of Patent: Aug. 26, 2003

(54) ELASTIC STRAND COATING PROCESS

(75) Inventor: Edward P. Erdman, Duluth, GA (US)

(73) Assignee: Paragon Trade Brands, Inc., Norcross, GA (US)

( * ) Notice: Subject to any disclaimer, the term of this patent is extended or adjusted under 35 U.S.C. 154(b) by 0 days.

(21) Appl. No.: 10/023,791

(22) Filed: Dec. 17, 2001

(65) Prior Publication Data

US 2003/0111162 A1 Jun. 19, 2003

(51) Int. Cl.[7] .......................... A61F 13/15; B32B 31/00
(52) U.S. Cl. ........................ 156/161; 156/229; 156/494; 156/578; 427/424; 118/324
(58) Field of Search .................... 156/161, 163, 156/164, 229, 578, 494; 427/207.1, 208.2, 208.4, 422, 424, 427; 118/325

(56) References Cited

U.S. PATENT DOCUMENTS

| | | | |
|---|---|---|---|
| 3,459,615 A | * | 8/1969 | Eilerman ............... 156/181 |
| 3,860,003 A | | 1/1975 | Buell |
| 4,081,301 A | | 3/1978 | Buell |
| 4,515,595 A | | 5/1985 | Kievit et al. |
| 4,646,362 A | | 3/1987 | Heran et al. |
| 4,764,242 A | * | 8/1988 | Gressick et al. ............ 156/494 |
| 4,795,454 A | | 1/1989 | Dragoo |
| 4,808,177 A | | 2/1989 | DesMarais et al. |
| 4,815,660 A | | 3/1989 | Boger |
| 4,816,025 A | | 3/1989 | Foreman |
| 4,880,420 A | | 11/1989 | Pomparelli |
| 4,938,755 A | | 7/1990 | Foreman |
| 5,098,423 A | | 3/1992 | Pieniak et al. |
| 5,147,487 A | | 9/1992 | Nomura et al. |
| 5,188,627 A | | 2/1993 | Igaue et al. |
| 5,281,207 A | | 1/1994 | Chmielewski et al. |
| 5,507,909 A | * | 4/1996 | Rollins et al. ............ 156/425 |
| 5,660,664 A | | 8/1997 | Herrmann |
| 5,745,922 A | | 5/1998 | Rajala et al. |
| 5,863,288 A | | 1/1999 | Baker |
| 5,870,778 A | | 2/1999 | Tharpe |
| 5,993,433 A | | 11/1999 | St. Louis et al. |
| 6,068,620 A | | 5/2000 | Chmielewski |
| 6,077,375 A | | 6/2000 | Kwok |
| 6,098,203 A | | 8/2000 | Rajala et al. |
| RE37,154 E | | 5/2001 | Nomura et al. |
| 6,235,137 B1 | | 5/2001 | Van Eperen et al. |
| 4,695,278 C1 | | 8/2001 | Lawson |

FOREIGN PATENT DOCUMENTS

EP        950436 A2   *  10/1999

* cited by examiner

Primary Examiner—Jeff H. Aftergut
(74) Attorney, Agent, or Firm—Hunton & Williams

(57) ABSTRACT

A method for applying a fluid filament to a strand useful for bonding elastic strands to an absorbent garment is described. The strand is oscillated as it moves along an isolated path past a fixed fluid filament dispenser. The strand captures substantially all of the fluid filament, and at least partially all sides of the strand are coated with the filament. The filament coated strand may then be bonded to one or more substrates in some embodiments.

49 Claims, 5 Drawing Sheets

ELASTIC STRAND COATING PROCESS

BACKGROUND OF THE INVENTION

1. Field of the Invention

The invention relates generally to adhesive dispersing systems and more particularly to processes and apparatus for bonding one or more relatively elongated strands to one or more substances, especially bonding stretched elastic strands to fabrics in the manufacture of absorbent garments.

2. Description of Related Art

Disposable absorbent garments such as infant diapers or training pants, adult incontinence products, and other such products are well-known in the art. Typically, the chassis of such garments comprises a liquid-permeable body-contacting liner sheet (or "topsheet"), a liquid-impermeable backing sheet (or "backsheet") (collectively the "sheets"), and a moisture-absorbent core fiber (or "absorbent core") that usually is made of a non-woven mat of randomly arranged fiber and is generally disposed between the topsheet and the backsheet.

These absorbent garments often times incorporate elastic elements in the waist, tummy and leg areas for improving the fit of the garment. The waist and tummy elastic elements increase the flexibility of the garment, allowing the same garment to accommodate a greater range of body sizes. In addition, they make the garment more form-fitting for the wearer. Leg gather elastic elements and standing leg gathers have also been employed to help reduce leakage of bodily exudates from the garment when the absorbent core cannot absorb body exudates fast enough. Leg gathers are known in the art, and U.S. Pat. No. 5,660,664 issued to Herman (the "'664 Patent") discloses an exemplary method of manufacturing leg gathers, the disclosure of which is incorporated by reference herein in its entirety.

These garments typically are prepared by continuously supplying the various components of the garment, and forming these components into the final garment. The elastic elements are continuously supplied at several different points of the assembly process, they typically are extended and then adhered to the garment components.

Typically the adhesive is sprayed onto stretched elastic strands disposed on or very near an underlying fabric substrate moving relative to one or more adhesive dispensing nozzles. The adhesive usually is a hot melt adhesive that is applied generously to both the substrate and the elastic strands simultaneously. Application of generous amounts of adhesive to substrate is often the result of inefficiency of application methods and does not typically provide bonding benefits. The stretched elastic strand is usually bonded between overlapping fabric layers. As the stretched elastic strands contracts, the fabric adhered thereto is bunched together forming generally pleated waist bands and other stretchable portions of the undergarment. It is important that the elastic strand be bonded to the fabric substantially continuously along its axial length to be bonded to ensure uniform pleating, or bunching, of the fabric, which is necessary for optimum comfort and fluid absorption, and to provide an aesthetically pleasing product.

Methods of bonding elastics to garment materials have been previously discussed in the art. An example of disposing elastic elements between layers of sheet material is provided in U.S. Pat. No. 5,870,778 issued to Tharpe, the disclosure of which is incorporated by reference herein in its entirety. Tharpe discloses coating the garment materials with adhesive to affix the elastic elements therein. A common procedure for affixing elastic elements in the industry today is a spiral spray adhesive application as disclosed in U.S. Pat. No. 4,815,660, issued to Boger, the disclosure of which is incorporated by reference herein in its entirety. Spiral spray adhesive application consists of ejecting a bead of hot melt adhesive, directing jets of pressurized air to form an elongated adhesive fiber from the bead, and imparting a rotational motion to the adhesive fiber. The spirals of adhesive are then deposited on the target substrate, typically a non-woven material. In usage, the adhesive spray coats not only the elastic elements but also "oversprays" to other sites, causing a number of undesirable consequences.

Some of these disadvantages include: The garment materials that are "oversprayed," e.g., portions of the topsheet, the bottom sheet, and the absorbent core, become rigid upon hardening of the "oversprayed" adhesive making the garment less comfortable for its wearer. This has been referred to as the "plywood effect." The "overspray" also may coat parts of the assembly machinery that must then be periodically cleaned of the adhesive. The elastic elements and/or the substrates to which they are to adhere may not be uniformly coated with the adhesive due to the nature of the spraying operation, and therefore the elastic elements may not bond to the garment materials as well as if they had been more uniformly and completely coated with the adhesive. Finally, the "overspray" is wasted adhesive, increasing the cost of materials for the finished garment.

Attempts have been made to reduce the amount of excess adhesive that is applied to the garment. U.S. Pat. No. 5,993,433 issued to St. Louis et al., which is incorporated herein by reference in its entirety, discloses an adhesive pattern for applying adhesives to the gathers, but such adhesive patterns still contribute to excessive garment stiffness and cost. U.S. Pat. No. 6,235,137 B1 issued to Van Eperen et al., which is incorporated herein by reference in its entirety, discloses a method of coating an elastic strand with a filament of adhesive, but this coating process is still subject to overspraying, and does not provide a complete coating of adhesive on the elastic.

In addition to stiffness and cost concerns, applying excess adhesive onto the elastic strands and underlying substrate than is required for bonding may, in the case of the typically used hot melt adhesives, have a tendency to deform the relatively thin, temperature sensitive fabric, thereby providing an undesirable appearance. In extreme cases the hot adhesive may destroy the fabric by burning a hole through the fabric.

Further excess adhesive applied onto the fabric may reduce the fluid absorbing capacity of the fabric and possibly result in the leakage of bodily fluids from the absorbent garment. Additionally, the adhesive stiffened fabric may be slightly abrasive against the skin, and in some extreme cases may irritate sensitive skin.

U.S. Pat. No. 5,507,909 to Rollins et al., (the "Rollins '909 Patent") discloses a process and apparatus for helically wrapping adhesive onto an elastic strand, which is bonded to a substrate in the manufacture of disposable absorbent products. The disclosure of the Rollins '909 patent is incorporated by reference herein in its entirety. To helically coat the elastic strand with adhesive, the strand is rotated about its axis as it is drawn past an adhesive flow from a dispensing orifice, for example by drawing the elastic strand between a nip roll assembly rotated at an angle relative thereto.

The process and apparatus disclosed in the Rollins '909 Patent allegedly reduces the amount of adhesive applied to the substrate and applies more conservative amounts of adhesive onto the elastic strand, but the uniform application of adhesive helically about the strand requires consistently and uniformly controlling the rotation of the strand during the drawing thereof. If the adhesive is not applied uniformly along the axial dimension of the strand, the stretched strand may not bond uniformly to the substrate, which adversely affects uniform bunching of the fabric. Non-uniform bunching is undesirable from an aesthetic viewpoint, and more substantively non-uniform bunching of the fabric compromises the ability of the fabric to form an effective fluid seal, and reduces the softness and comfort thereof when stretched against the wearer's body.

U.S. Pat. No. 6,077,375 to Kwok (the "Kwok '375 Patent") discloses applying fluids including adhesives onto strands. More particularly the Kwok '375 Patent discloses methods for applying fluids to a strand, useable for bonding the strand to a substrate in the production of bodily fluid absorbing hygienic articles, by drawing the strand along an isolated path, moving a fluid fiber across a path of the strand as the fluid fiber is dispensed toward the strand so that the fiber contacts the strand, and substantially all of the fiber is captured on the isolated strand. The disclosure of the Kwok '375 Patent is incorporated by reference herein in its entirety. The fiber is oscillated back and forth across a path of the strand, and beyond opposing sides thereof to at least partially coat all sides thereof with fluid.

In an exemplary application of the method disclosed in the Kwok '375 Patent, the fluid fiber is a substantially continuous hot melt adhesive fiber dispensed from an adhesive orifice. The adhesive fiber oscillates back and forth across the path of an elastic strand and beyond opposing sides thereof under the influence of first and second air flows dispensed from first and second air orifices disposed on opposing sides of a corresponding adhesive orifice.

The amplitude and frequency of oscillation of adhesive fibers is controlled by the first and second air flows. In an alternative embodiment, the '375 Patent describes dispensing hot melt adhesive fibers from a spiral nozzle in a swirling pattern to move the adhesive fiber back and forth across the path of the strand as the adhesive fiber is dispensed toward the strand. The use of air jets near the adhesive dispensing nozzle as described in the '375 Patent may lead to clogging of the adhesive dispensing nozzle or dispense adhesive fumes in the manufacturing environment or both.

The foregoing description of the various products, methods, and apparatus, and their attendant disadvantages is in no way intended to limit the scope of the present invention, or to imply that the present invention does not include some or all of the various elements of the products, methods, and apparatus in one form or another. Indeed, various embodiments of the invention may be capable of overcoming some of the disadvantages, while still retaining some or all of the various elements of the products, methods, and apparatus in one form or another.

SUMMARY OF INVENTION

There exists a need to manufacture a softer absorbent garment that has not had materials "oversprayed" with adhesive during coating of the elastic elements for assembly. A need also exists for a clean, more efficient, cost effective method of applying adhesive to the elastic elements for assembly into an absorbent garment. Additionally, a need exists to more uniformly and completely coat elastic elements with adhesive prior to bonding to an absorbent garment to promote product uniformity and improved adhesion of the elastic elements to the garment. Further, a need exists to reduce the use of air jets near adhesive application nozzles to improve maintenance requirements, and to improve environmental aspects of the manufacturing area.

It therefore is a feature of various embodiments of the invention to address the aforementioned needs by providing a method for discretely coating elastic strands with fluid adhesive fibers prior to incorporation of the elastic strands into absorbent garments. In accordance with these and other features of the invention, there is provided a method for applying a fiberized fluid adhesive to a strand that comprises: supplying a strand along a machine direction; dispensing a substantially continuous fluid adhesive fiber toward the strand in a direction normal to the machine direction; oscillating the strand back and forth in a direction orthogonal to the machine direction, and in a plane normal to the continuous fluid adhesive fiber across the path of the fluid adhesive fiber as the fluid adhesive fiber is dispensed toward the strand; capturing substantially all of the continuous fluid adhesive fiber on the strand; and coating all sides of the strand at least partially with the fluid adhesive fiber. In one exemplary embodiment, dispensing the continuous fluid adhesive fiber is initiated and terminated at predetermined intervals.

In accordance with another embodiment of the invention, there is provided a method of bonding a strand to a substrate comprising: drawing the strand along a path separated spatially from a first substrate; dispensing the fluid adhesive fiber from above the strand; capturing substantially all of the fluid adhesive fiber on the strand when the strand is spatially separated from the first substrate; coating all sides of the strand at least partially with the adhesive fiber when the strand is spatially separated from the first substrate; and contacting the adhesive coated strand with the substrate to bond the strand to the first substrate. A method of making a laminate also is disclosed whereby during or after the adhesive coated strand is bonded to the first substrate, a second substrate is provided so that the adhesive coated strand is disposed between the first and second substrates.

In another exemplary embodiment of the invention, the method may comprise supplying a plurality of strands separated spatially from a substrate and from each other in a machine direction, dispensing a plurality of adhesive fibers from a corresponding plurality of adhesive orifices toward a corresponding one of the plurality of strands; oscillating each of the plurality of strands back and forth in a direction orthogonal to the machine direction, and in a plane normal to the continuous fluid adhesive fiber across the path of the corresponding adhesive fibers as the fluid adhesive fibers are dispensed toward the strands, capturing substantially all of each adhesive fiber on the corresponding strand when the strand is substantially separated from the substrate, at least partially coating all sides of each strand with the corresponding adhesive fiber when the strand is spatially separated from the substrate; and contacting the plurality of adhesive coated strands with the substrate to bond the plurality of strands to the substrate.

In one preferred embodiment the method described above is used for applying adhesive to a strand for bonding the strand to a substrate in the manufacture of an absorbent garment. In another preferred embodiment, the strand is a strand of elastic material.

The invention further includes an apparatus for applying fluid filaments to a strand, a method and apparatus for making a laminate including two outer layers having a strand disposed there between, and a method and apparatus for forming an absorbent garment. The apparatus for applying fluid filaments to a strand comprises: a dispensing nozzle for dispensing fluid filaments to a strand; a strand supply mechanism for supplying a strand in a machine direction that is substantially normal to the path of the fluid filament dispensed from the dispensing nozzle; and a mechanism for oscillating the strand in a direction orthogonal to the machine direction, and in a plane substantially orthogonal to the path of the fluid filament.

The apparatus for making a laminate comprises, in addition to the apparatus described above for applying fluid filaments to a strand, a first substrate supply mechanism for supplying a first substrate in the machine direction, whereby the strand is positioned between the dispensing nozzle and the first substrate. The apparatus further includes a second substrate supply mechanism for supplying a second substrate such that the strand is disposed between the first substrate and the second substrate, and a mechanism for bringing the first substrate, strand, and second substrate together to form a laminate.

In accordance with another feature of an embodiment of the invention, there is provided a method of making an absorbent garment that includes providing a top sheet material, a back sheet material, and an absorbent core. The method also includes applying a fluid filament to a strand in accordance with the method described above, and disposing fluid filament-coated strand and the absorbent core between the top sheet material and the back sheet material.

In accordance with another feature of an embodiment of the invention, there is provided a method of making an absorbent garment that includes providing a top sheet material, a back sheet material, and an absorbent core, and disposing the absorbent core between the top sheet material and the back sheet material to form an absorbent core assembly. The method also includes making a laminate that includes a first substrate, a second substrate, and a strand disposed between the first and second substrates in accordance with the method described above. The method also includes attaching the laminate to the absorbent core assembly.

In accordance with another feature of an embodiment of the invention, there is provided an apparatus for forming an absorbent garment that includes a top sheet supply mechanism, a back sheet supply mechanism, and an absorbent core supply mechanism for supplying each of the respective components to a forming station. The apparatus further includes either the apparatus for applying a fluid filament to a strand or the apparatus for making a laminate as described above, or both. The apparatus includes further a forming station for disposing the absorbent core and fluid filament-coated strand between the top sheet material and the back sheet material. The forming station may also optionally have a laminated attachment station that is capable of attaching the optional laminate to either the backsheet material, the top sheet material, or both.

BRIEF DESCRIPTION OF THE DRAWINGS

The invention may be understood more readily by reviewing the drawings, in which.

DETAILED DESCRIPTION OF PREFERRED EMBODIMENTS

Figure 1:
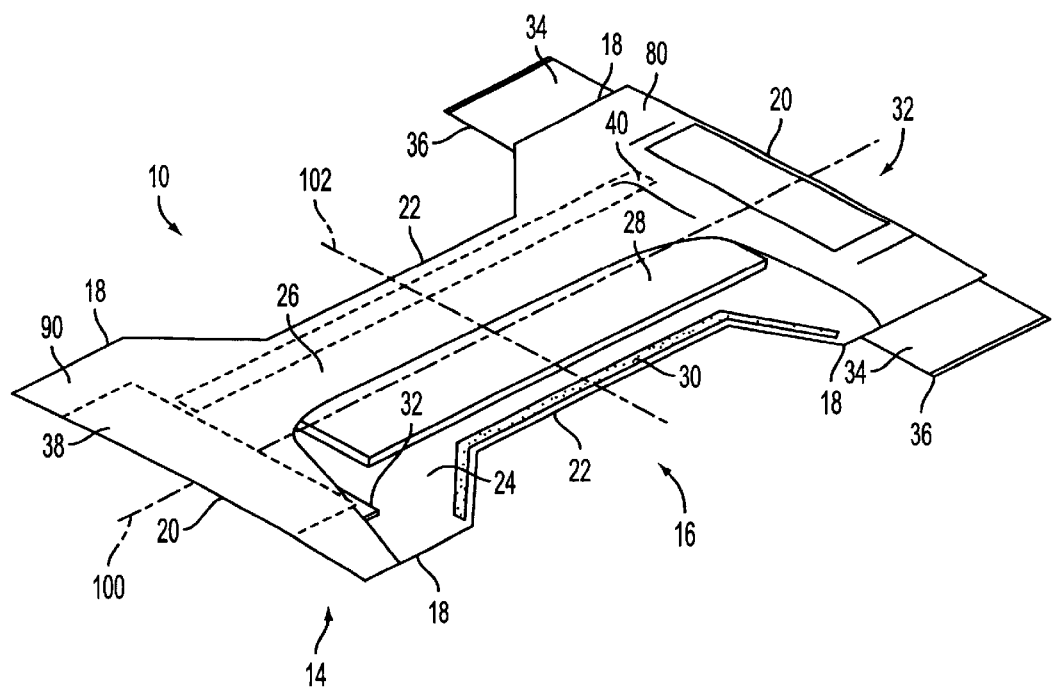
FIG. 1 shows a partially cut away view of an exemplary embodiment of an absorbent garment.

One advantage of an embodiment of the invention is that by discretely coating the elastic elements before bonding them to the sheets of the absorbent garments, or to the outer sheets of a laminate material, the sheets and absorbent core are not inadvertently coated with adhesive that typically occurs when the adhesive is applied by spraying. The sheets and absorbent core therefore retain their original softness and pliability, rather than becoming partially rigid through the adhesive "overspray" that stiffens these materials upon hardening of the adhesive.

A further advantage of the invention is that the elastic elements may be discretely coated (i.e., coated along discrete portions of their length while leaving other portions uncoated) with a high accuracy as compared to conventional coating methods.

Another advantage of the invention is that the discretely coated elastic elements are more uniformly and completely coated with adhesive, resulting in more effective and uniform bonding of the elastic elements to the sheets of the garment. In an embodiment in which the elastics are attached between laminated sheets or within a fold of a sheet, no other bonding between the sheets may be necessary to maintain the integrity of the lamination on the fold.

Yet another advantage of the invention is a cost savings in adhesive, as the present system and methods results in a reduction in the amount of adhesive required to form an absorbent garment when compared to a garment prepared using the known spraying techniques.

Another advantage of the invention is that it avoids the need for air jets to direct the position of the adhesive filament.

Yet another advantage of the invention is a cleaner work environment, and less cost for clean up of the assembly machinery as the adhesive is no longer errantly sprayed onto the assembly of the surrounding work area.

The invention provides a method for applying a fiberized fluid adhesive to a strand. The method includes supplying a strand in a machine direction; dispensing a substantially continuous fluid adhesive fiber toward the strand; and in a direction normal to the machine direction; oscillating the strand back and forth in a direction orthogonal to the machine direction, and in a plane normal to the continuous fluid adhesive fiber, across the path of the fluid adhesive fiber as the fluid adhesive fiber is dispensed toward the strand; capturing substantially all of the continuous fluid adhesive fiber on the strand; and coating all sides of the strand at least partially with the fluid adhesive fiber.

The method for applying a fiberized fluid may also include oscillating the strand predominately transversely to the path of the fluid adhesive fiber and beyond opposing sides of adhesive fluid fiber as the adhesive fluid fiber is dispensed toward the strand, thereby wrapping portions of fluid adhesive fiber about the strand. In some embodiments the fluid adhesive fiber is a hot melt adhesive and the strand is an elastic strand.

The method may further comprise drawing the strand along a path separated spatially from a first substrate; dispensing the fluid adhesive fiber from above the strand; capturing substantially all of the fluid adhesive fiber on the strand when the strand is spatially separated from the first substrate, coating all sides of the strand at least partially with the adhesive fiber when the strand is spatially separated from the first substrate, and contacting the adhesive coated strand with the substrate to bond the strand to the first substrate.

The strand may be separated from the first substrate by a distance greater than a droop distance of the adhesive fiber below the strand where the adhesive is dispensed to the strand.

The method may further comprise stretching the elastic before bonding the elastic strand to the first substrate.

In some embodiments the method may further include bonding the adhesive coated strand to a second substrate thereby disposing the strand between the first substrate and the second substrate to form a laminate.

In one exemplary embodiment dispensing of the substantially continuous fluid adhesive filament is initiated and terminated at predetermined intervals.

In some embodiments the method may include supplying a plurality of strands in the machine direction separated spatially from a substrate and from each other, dispensing a plurality of adhesive fibers from a corresponding plurality of adhesive orifices toward a corresponding one of the plurality of strands; oscillating each of the plurality of strands back and forth in a direction orthogonal to the machine direction, and in a plane normal to the continuous fluid adhesive fiber across the path of the corresponding adhesive fibers as the fluid adhesive fibers are dispensed toward the strands; capturing substantially all of each adhesive fiber on the corresponding strand when the strand is substantially separated from the substrate; at least partially coating all sides of each strand with the corresponding adhesive fiber when the strand is spatially separated from the substrate; and contacting the plurality of adhesive coated strands with the substrate to bond the plurality of strands to the substrate.

The invention provides for applying adhesive to a strand for bonding the strand, or alternatively, to a plurality of strands and for bonding the plurality of strands to a substrate for use in the production of an absorbent garment. The adhesive is applied to the strand(s) using the method for applying a fiberized fluid adhesive to a strand disclosed above. In some embodiments the adhesive is a hot melt adhesive. In some embodiments the strands are elastic strands.

The invention further provides an absorbent garment manufacturing system comprising a first path for supplying a first layer of material; a second path for supplying a second layer of material; a third path for supplying one or more elastic strands; and an applicator for dispensing adhesive to the one or more elastic strands. The applicator dispenses one or more adhesive filaments to corresponding one or more elastic strands, the one or more elastic strands are spatially separated from the first and second layers of material when the adhesive filament is disposed on the elastic strand, and the one or more elastic strands oscillates back and forth across the path of the adhesive filament as the adhesive fiber is dispensed toward the elastic strand.

The invention also provides an apparatus for applying fluid filaments to a strand that includes a dispensing nozzle for dispensing fluid filaments to a strand; a strand supply mechanism for supplying a strand in a machine direction that is substantially normal to the path of the fluid filament dispensed from the dispensing nozzle; and a mechanism for oscillating the strand in a direction orthogonal to the machine direction, and in a plane substantially orthogonal to the path of the fluid filament.

The invention provides further an apparatus for making a laminate that includes, in addition to the apparatus described above for applying fluid filaments to a strand, a first substrate supply mechanism for supplying a first substrate in the machine direction, whereby the strand is positioned between the dispensing nozzle and the first substrate. The apparatus further includes a second substrate supply mechanism for supplying a second substrate such that the strand is disposed between the first substrate and the second substrate, and a mechanism for bringing the first substrate, strand, and second substrate together to form a laminate.

The invention also provides a method of making an absorbent garment that includes providing a top sheet material, a back sheet material, and an absorbent core. The method also includes applying a fluid filament to a strand in accordance with the method described above, and disposing fluid filament-coated strand and the absorbent core between the top sheet material and the back sheet material.

The invention provides further a method of making an absorbent garment that includes providing a top sheet material, a back sheet material, and an absorbent core, and disposing the absorbent core between the top sheet material and the back sheet material to form an absorbent core assembly. The method also includes making a laminate that includes a first substrate, a second substrate, and a strand disposed between the first and second substrates in accordance with the method described above. The method also includes attaching the laminate to the absorbent core assembly.

Another embodiment of the invention includes an apparatus for forming an absorbent garment that includes a top sheet supply mechanism, a back sheet supply mechanism, and an absorbent core supply mechanism for supplying each of the respective components to a forming station. The apparatus further includes either the apparatus for applying a fluid filament to a strand or the apparatus for making a laminate as described above, or both. The apparatus includes further a forming station for disposing the absorbent core and fluid filament-coated strand between the top sheet material and the back sheet material. The forming station also is capable of attaching the optional laminate to either the backsheet material, the top sheet material, or both.

As used herein, the term "absorbent garment" refers to garments that absorb and contain exudates, and more specifically, refers to garments, which are placed against or in proximity to the body of the wearer to absorb and contain the various exudates discharged from the body. A nonexhaustive list of examples of absorbent garments includes diapers, diaper covers, disposable diapers, training pants, feminine hygiene products and adult incontinence products. The term "disposable absorbent garment" refers to absorbent garments that are intended to be discarded or partially discarded after a single use (i.e., they are not intended to be laundered or otherwise restored or reused). The term "unitary disposable absorbent garment" refers to a disposable absorbent garment that is essentially a single structure (i.e., it does not require separate manipulative parts such as a diaper cover and insert). As used herein, the term "diaper" refers to an absorbent garment generally worn by infants and incontinent persons about the lower torso.

The claims are intended to cover all of the foregoing classes of absorbent garments, without limitation, whether disposable, unitary or otherwise. These classifications are used interchangeably throughout the specification, but are not intended to limit the claimed invention. The invention will be understood to encompass, without limitation, all classes of absorbent garments, including those described above. Preferably, the absorbent core is thin in order to improve the comfort and appearance of a garment. The importance of thin, comfortable garments is disclosed, for example, in U.S. Pat. No. 5,098,423 to Pieniak et al., which is herein incorporated by reference.

Throughout this description, the expressions "upper layer," "lower layer," "above" and "below," which refer to the various components included in the absorbent core units of the invention (including the layers surrounding the absorbent core units) are used merely to describe the spatial relationship between the respective components. The upper layer or component "above" the other component need not always remain vertically above the core or component, and the lower layer or component "below" the other component need not always remain vertically below the core or component. Indeed, embodiments of the invention include various configurations whereby the core or laminate is folded in such a manner that the upper layer ultimately becomes the vertically highest and vertically lowest layer at the same time. Other configurations are contemplated within the context of the present invention.

The term "component" can refer, but is not limited, to designated selected regions, such as edges, corners, sides or the like; structural members, such as elastic strips, absorbent pads, stretchable layers or panels, layers of material, or the like; or a graphic.

Throughout this description, the term "disposed" and the expressions "disposed on," "disposing on," "disposed in," "disposed between" and variations thereof (e.g., a description of the article being "disposed" is interposed between the words "disposed" and "on") are intended to mean that one element can be integral with another element, or that one element can be a separate structure bonded to or placed with or placed near another element. Thus, a component that is "disposed on" an element of the absorbent garment can be formed or applied directly or indirectly to a surface of the element, formed or applied between layers of a multiple layer element, formed or applied to a substrate that is placed with or near the element, formed or applied within a layer of the element or another substrate, or other variations or combinations thereof.

Throughout this description, the terms "top sheet" and "back sheet" denote the relationship of these materials or layers with respect to the absorbent core. It is understood that additional layers may be present between the absorbent core and the top sheet and back sheet, and that additional layers and other materials may be present on the side opposite the absorbent core from either the top sheet or the back sheet.

Absorbent garments and diapers may have a number of different constructions. In each of these constructions it is generally the case that an absorbent core is disposed between a liquid pervious body-facing top sheet, and a liquid impervious, exterior facing back sheet. In some cases, one or both the top sheet and the back sheet may be shaped to form a pant-like garment. In other cases, the top sheet, back sheet and absorbent core may be formed using a discreet assembly that is placed on a main chassis and the chassis is made to form a pant-like garment. In the case of diapers, a caregiver usually wraps the diaper around the wearer's waist and joins the side seams manually by attaching one or more adhesive or mechanical tabs, thereby making the pant-like structure. In the case of training pant-type garments and most adult incontinent products, the garment is provided fully formed with factory made side seams and the garment is donned by pulling it up the wearer's leg. For clarity, the present invention is described herein, only with reference to the diaper type garment, although the invention may be used with other constructions having elastics incorporated therein including for example, the training pant-type garments, adult and incontinent products or feminine hygiene products.

The invention now will be described with reference to the attached drawings illustrating preferred embodiments of the invention. For clarity, features that appear in more than one Figure have the same reference number in each Figure.

FIG. 1 is a partially cut away depiction of an exemplary embodiment of an absorbent garment 10 (preferably a disposable absorbent garment) of the present invention. The embodiment shown in FIG. 1 is an infant's diaper, however, this depiction is not intended to limit the invention, and those skilled in the art appreciate that the invention covers other types of absorbent articles. For simplicity, however, the invention will be described with reference to an infant's diaper. The garment 10 of FIG. 1 is depicted in a generally flattened position, with the body-facing side facing down, and with the various elastic components depicted in their relaxed condition with the effects of the elastics removed for clarity (when extended, the elastics typically cause the surrounding material to gather or "shirr"). In the flattened position, the garment 10 may have a generally hourglass shaped structure, but it may also have any other shape suitable for the given application, such as a rectangular shape, a trapezoidal shape, a "T" shape, and the like.

As used herein, the longitudinal axis 100 of the garment is the dimension of the garment corresponding to the front-to-rear dimension of the user, and the lateral axis 102 of the garment is the dimension corresponding to the side-to-side dimension of the user.

In use, the invention comprises a pant-like garment 10 having a waist-encircling region and a crotch region. The waist-encircling region may comprise a first waist region 12, disposed adjacent to, for example, the back waist region of a wearer's body, and a second waist region 14, disposed adjacent to, for example, the front waist region of a wearer's body. The first and second waist regions 12, 14, may correspond to the front and back of the wearer's body, respectively, depending on whether garment 10 is attached in front of or behind the subject wearer. The first and second waist regions are joined together at or near their lateral edges 18, causing the longitudinally distal edges 20 of the garment 10 to form the perimeter of a waist opening. A crotch region 16 extends between the first and second waist regions 12, 14, and the crotch edges 22 forms the perimeter of a pair of leg openings, when the garment 10 is placed on a subject wearer.

The garment 10 preferably comprises a top sheet 24, and a back sheet 26, which may be substantially coterminous with the top sheet 24. When the garment 10 is being worn, the top sheet 24 faces the wearer's body, and the back sheet 26 faces away from the wearer. An absorbent core 28 preferably is disposed between at least a portion of the top sheet 24 the back sheet 26.

An embodiment of the present invention may further comprise various additional features. One or more pairs of elastic gathers 30 may extend adjacent the crotch edges 22 or a portion thereof. The garment 10 may also comprise one or more waste containment systems, such as inboard standing leg gathers 40, which preferably extend from the second waist region 14 to the first waist region 12 along opposite sides of longitudinal center line 100 (only one standing leg gather system 40 is shown in FIG. 1 for purposes of clarity). One or both of the first and second waist regions 12, 14 may also be equipped with strips of elastic waist foam 32 or other elastically extensible material, which help contract the garment around the wearer's waist, providing improved fit, leakage protection and aesthetics.

The absorbent garment 10 also preferably includes fastening elements to enable attachment of the first waist region 12 to second waist region 14. Fastening elements preferably include a pair of tabs 34 that extend laterally away from opposite lateral edges 18 of the first waist region 12 of the garment 10. The tabs 34 may be extensions of one or more components of the body of the garment or the tabs 34 may be formed as tab components and attached to the body of the garment, for example. The tabs 34 may in some embodiments comprise an elastically extensible material (not shown), and may be designed to stretch around a wearer's waist to provide improved fit, comfort, and leakage protection. Such elasticized tabs 34 may be used in conjunction with, or in lieu of, waist foam 32, or other elastically extensible materials 32.

At least one fastening mechanism 36 (collectively referred to as "fastener 36") is attached to each tab 34 for attaching the tab to the second waist region 14, thereby providing the garment 10 with a pant-like shape, and enabling garment 10 to be fixed or otherwise fitted on the wearer. The fasteners 36 may attach to one or more target devices 38 located in the second waist region 14.

Although not shown in the drawings, the absorbent garment 10 may also include grips (in some embodiments referred to as finger lifts) attached along one of its edges proximal to each tab 34 to enable a caregiver to pull the grips, and not on the ends of the tabs 34, around the wearer and over the target devices 38 to thereby secure the fasteners 36 to the one or more target devices 38.

The various parts of the garment 10 can be attached to one another or associated with one another to form a structure that preferably maintains its shape during the useful life of the garment 10. As used herein, the terms "attached," "joined," "associated," and similar terms encompass configurations whereby a first part is directly joined to a second part by affixing the first part directly to the second part, by indirectly joining the first part to the second part through intermediate members, and by fixing the relative positions of various parts by capturing parts between other parts. Those skilled in the art will appreciate that various methods or combinations of methods may be used to securely join the respective parts of the garment 10 to one another.

The top sheet 24 and back sheet 26 may be constructed from a wide variety of materials known in the art. Due to the wide variety of backing and liner sheet construction and materials currently available, the invention is not intended to be limited to any specific materials or constructions of these components. The top sheet 24 and back sheet 26 can be shaped and sized according to the requirements of each of the various types of absorbent garment, or to accommodate various user sizes. In an embodiment of the invention in which the garment 10 is a diaper or an adult incontinence brief, the combination of top sheet 24 and back sheet 26, may have an hourglass shape, as seen in FIG. 1, or may have a rectangular, trapezoidal, "T" shape, or other shape.

The back sheet 26 preferably is made from any suitable pliable liquid-impervious material known in the art. Typical back sheet materials include films of polyethylene, polypropylene, polyester, nylon, and polyvinyl chloride and blends of these materials. For example, the back sheet can be made of a polyethylene film having a thickness in the range of 0.01–0.03 mm. The back sheet 26 may be pigmented with, for example, titanium dioxide, to provide the garment 10 with a pleasing color or to render the back sheet 26 opaque enough that exudates being contained by the garment 10 are not visible from outside the garment. In addition, the back sheet 26 may be formed in such a manner that it is opaque, for example, by using various inert components in the polymeric film. Other back sheet materials will be readily apparent to those skilled in the art. The back sheet 26 preferably has sufficient liquid imperviousness to prevent any leakage of fluids. The required level of liquid imperviousness may vary between different locations on the garment 10.

The back sheet 26 may further comprise separate regions having different properties. In a preferred embodiment, portions of the back sheet 26 are air-permeable to improve the breathability, and therefore comfort, of the garment 10. The different regions may be formed by making the back sheet 26 a composite of different sheet materials, chemical treatment, heat treatment, or other processes or methods known in the art. Some regions of the back sheet 26 may be fluid pervious. In one embodiment of the invention, the back sheet 26 is fluid impervious in the crotch 16, but is fluid pervious in portions of the first and second waist regions 12, 14. The back sheet 26 may also be made from a laminate of overlaid sheets of material.

The moisture-pervious top sheet 24 can be comprised of any suitable relatively liquid-pervious material known in the art that permits passage of liquid there through. Non-woven liner sheet materials are exemplary because such materials readily allow the passage of liquids to the underlying absorbent core 28. Examples of suitable liner sheet materials include non-woven spun-bond or carded webs of polypropylene, polyethylene, nylon, polylactic acid (PLA), polyester and blends of these materials. Alternatively, woven or apertured films may be used.

The back sheet 26 may be covered with a fibrous, non-woven fabric such as is disclosed, for example, in U.S. Pat. No. 4,646,362 issued to Heran et al., the disclosure of which is hereby incorporated by reference in its entirety and in a manner consistent with this disclosure. Materials for such a fibrous outer liner include a spun-bonded non-woven web of synthetic fibers such as polypropylene, polyethylene or polyester fibers; a non-woven web of cellulosic fibers, textile fibers such as rayon fibers, cotton and the like, or a blend of cellulosic and textile fibers; a spun-bonded non-woven web of synthetic fibers such as polypropylene; polylactic acid (PLA), polyethylene or polyester fibers mixed with cellulosic, pulp fibers, or textile fibers; or melt blown thermoplastic fibers, such as macro fibers or micro fibers of polypropylene, polyethylene, polyester or other thermoplastic materials or mixtures of such thermoplastic macro fibers or micro fibers with cellulosic, pulp or textile fibers. Alternatively, the back sheet 26 may comprise three panels wherein a central poly back sheet panel is positioned closest to absorbent core 28 while outboard non-woven breathable side back sheet panels are attached to the side edges of the central poly back sheet panel. Alternatively, the back sheet 26 may be formed from microporous poly coverstock for added breathability.

The top sheet 24 may be formed of three separate portions or panels. Those skilled in the art will recognize, however, that top sheet 24 need not be made of three separate panels, and that it may be comprised of one unitary item. A first top sheet panel (not shown) may comprise a central top sheet panel formed from preferably a liquid-pervious material that is either hydrophobic or hydrophilic. The central top sheet panel may be made from any number of materials, including synthetic fibers (e.g., polypropylene or polyester fibers), natural fibers (e.g., cotton, wood or cellulose), apertured plastic films, reticulated foams and porous foams to name a few. One preferred material for a central top sheet panel is a cover stock of single ply non-woven material which may be made of carded fibers, either adhesively or thermally bonded, perforated plastic film, spun-bonded fibers, or water entangled fibers, which generally weigh from 0.3–0.7 oz./sq. yd. and have appropriate and effective machine direction and cross-machine direction strength suitable for use as a baby diaper cover stock material. The central top sheet panel preferably extends from substantially the second waist region 14 to the first waist region 12, or a portion thereof.

A second and third top sheet panels (e.g., outer top sheet panels, not shown), in this alternative embodiment may be positioned laterally outside of the central top sheet panel. The outer top sheet panels preferably are substantially liquid-pervious at least in the crotch area. In other embodiments, portions of the outer top sheet panels may be liquid-impervious and hydrophobic. The outer edges of the outer top sheet panels may substantially follow the corresponding outer perimeter of the back sheet 26. The material for the outer top sheet portions or panels is preferably polypropylene and can be woven, non-woven, spun-bonded, carded or the like, depending on the application. The second and third top sheet panels may in some embodiments contribute desirable aesthetic characteristics.

At the point of connection between the outer top sheet panels and the central top sheet panel, inner edges of the outer top sheet portions or panels may extend upwardly to form waste containment flaps 40. The waste containment flaps 40 preferably are formed of the same material as the outer top sheet portions or panels, as in the embodiment shown. The waste containment flaps 40 may be treated with a suitable surfactant to modify their hydrophobicity/hydrophilicity as desired, and they may be treated with skin wellness ingredients to reduce skin irritation. Alternatively, the waste containment flaps 40 may be formed as separate elements and then attached to the body side liner.

The waste containment flaps 40 preferably include a portion that folds over onto itself to form a small enclosure. At least one, and depending on the size of the enclosure sometimes more than one, elastic member may be secured in the enclosure in a stretched condition. When the flap elastic attempts to assume the relaxed, unstretched condition, the waste containment flaps 40 rise above the surface of the central top sheet portion or panel.

The top sheet 24 may be made of any suitable relatively liquid-pervious material currently known in the art or later discovered that permits passage of a liquid there through. Examples of suitable top sheet materials include nonwoven spun-bonded or carded webs of polypropylene, polyethylene, nylon, rayon, rayon derivatives, polylactic acid (PLA), polyester and blends of these materials, perforated, apertured, or reticulated films, and the like. Non-woven materials are exemplary because such materials readily allow the passage of liquids to the underlying absorbent core 28. The top sheet 24 preferably comprises a single-ply non-woven material that may be made of carded fibers, either adhesively or thermally bonded, spun-bonded fibers, or water entangled fibers, which generally weigh from 0.3–0.7 oz./sq. yd. and have appropriate and effective machine direction (longitudinal) and cross-machine (lateral) direction strength suitable for use as a top sheet material for the given application. The present invention is not intended to be limited to any particular material for the top sheet 24, and other top sheet materials will be readily apparent to those skilled in the art.

The top sheet 24 may further comprise several regions having different properties. In one embodiment of the present invention, the laterally distal portions of the top sheet 24, especially those used to make the outer top sheet panels preferably are substantially fluid impervious and hydrophobic, while the remainder of the top sheet 24 (e.g., central top sheet panel) is hydrophilic and fluid pervious. Different top sheet properties, such as fluid perviousness and hydrophobicity, may be imparted upon the top sheet 24 by treating the top sheet 24 with adhesives, surfactants, or other chemicals, using a composite of different materials, or by other means. The top sheet 24 may also be made from a laminate of overlaid sheets of material. The top sheet 24 also may be treated as a whole or in specific areas like the crotch region, with skin wellness ingredients such as aloe, vitamin E, and the like.

As noted elsewhere herein, the top sheet 24 and back sheet 26 may be substantially coterminous, or they may have different shapes and sizes. The particular design of the top sheet 24 and back sheet 26 may be dictated by manufacturing considerations, cost considerations, and performance considerations. Preferably, the top sheet 24 is large enough to completely cover the absorbent core 28, and the back sheet 26 is large enough to prevent leakage from the garment 10. The design of top sheet 24 and back sheet 26 is known in the art, and a skilled artisan will be able to produce an appropriate top sheet 24 and an appropriate back sheet 26 without undue experimentation.

The top sheet 24 and the back sheet 26 may be associated with one another using a variety of methods known in the art. For example, they may be thermally, ultrasonically, or chemically bonded to one another. They also may be joined using lines of hot melt adhesive or mechanical fasteners, such as thread, clips, or staples. In one embodiment, a hydrophilic adhesive, such as Cycloflex as sold by National Starch, a corporation headquartered in Bridgewater, N.J., is used to join the top sheet 24 to the back sheet 26. The particular joining method may be dictated by the types of materials selected for the top sheet 24 and back sheet 26.

As mentioned above, the absorbent garment preferably is provided with leg elastics 30 extending through crotch region 16, adjacent crotch edge 22. The absorbent garment of the invention also preferably is provided with waist elastic material 32 optionally in the first and second waist regions, 12, 14, respectively, to enable and assist in stretching around the wearer. The waist elastics 32 may be similar structures or different to impart similar or different elastic characteristics to the first and second waist regions 12, 14 of the garment. In general, the waist elastics may preferably comprise foam strips positioned at the first and second waist regions 12, 14, respectively. Such foam strips preferably are about ½ to about 1½ inches in the dimension substantially parallel with longitudinal axis 100 and about 3–6 inches in the dimension substantially parallel with the lateral axis 102. The foam strips preferably are positioned between the top sheet 24 and the back sheet 26. Alternatively, a plurality of elastic strands may be employed as waist elastics rather than foam strips. The foam strips preferably are comprised of polyurethane, but can be any other suitable material that decreases waist band roll over, reduces leakage over the waist ends of the absorbent garment, and generally improve comfort and fit. The first and optional second waist foam strips 32 preferably are partially or completely stretched 50–150%, preferably 100% more than their unstretched dimension before being adhesively secured between the back sheet 26 and top sheet 24. U.S. Pat. No. 4,515,595 to Kievit et al. and U.S. Pat. No. 4,816,025 to Foreman illustrate other embodiments of elasticized waist features of absorbent garments, and are hereby incorporated by reference in their entirety.

Each edge 22 that forms the leg openings preferably is provided with an adjacent leg elastic containment system 30. In an exemplary embodiment, three strands of elastic threads are positioned to extend adjacent to leg openings between the top sheet 24 and the back sheet 26. Any suitable elastomeric material exhibiting at least an elongation (defined herein as $(L_S-L_R)/L_R$ where $L_S$ is the stretch length of an elastic element and $L_R$ is retracted length, multiplied by 100 to obtain percent elongation) in the range of 5%–500%, preferably in the range of 200%–400%, can be employed for the leg elastics 30. The leg elastics 30 may be attached to the absorbent article 10 in any of several ways, which are known in the art. For example, the leg elastics 30 may be ultrasonically bonded, heat/pressure sealed using a variety of bonding patterns, or glued to the garment 10 with hot melt adhesives, construction adhesives and the like. Various commercially available materials can be used for the elastics, such as natural rubber, butyl rubber or other synthetic rubber, urethane, elastomeric materials such as LYCRA (DuPont), GLOSPAN (RadiciSpandex) or SYSTEM 7000 (Fulflex).

Additional elastics (not shown) may also be incorporated into the topsheet 24 or backsheet 26 adjacent the leg holes to form conventional (i.e., non-standing) leg gathers, as is known in the art. Conventional gathers contract the garment 10 around the wearer's legs and body to prevent leakage. U.S. Pat. Nos. 3,860,003 and 4,081,301 issued to Buell, U.S. Pat. No. 4,695,278 issued to Lawson, U.S. Pat. No. 4,808,177 issued to Des Marais, U.S. Pat. No. 4,795,454 issued to Dragoo, and U.S. Pat. No. 4,938,755 issued to Foreman illustrate other embodiments of leg cuffs and gathers in absorbent garments, and the disclosures of each of these patents are hereby incorporated by reference in their entirety.

It is often desirable for an absorbent garment to contract around various parts of the wearer's body to provide improved comfort and exudate containment. In addition to the leg gathers 30 and waist elastic 32, tummy elastics (not shown) may be incorporated into the garment 10 to contract the garment 10 about the wearer's waist and stomach. Such elastics are typically stretched as they are joined to the garment 10 so that the contraction of the elastics causes the garment 10 to contract about the wearer. The elastics may also be applied in an unstretched state then mechanically stretched to create an elasticized region (often called a zero-strain laminate). The elastics may also be applied in an inelastic state then heat activated to cause them to become elasticized. The tummy elastics may be made from material as synthetic rubber, elastomers, LYCRA® elastomers (available from E. I. DuPont du Nemours and Company, a business having offices in Wilmington, Del.), polyurethane, heat shrinkable polymer ribbons or any other suitable elastic material or composite.

The fastening elements, preferably a fastening system 34 (e.g., tab 34) of the preferred embodiment, is attached to the first waist region 12, and it preferably comprises a tape tab or mechanical fasteners 36. However, any fastening mechanism known in the art will be acceptable. Moreover, the fastening system 34 may include a landing zone or attachment area 38 preferably provided in the second waist region 14 to permit attachment of the first waist region 12 to the second waist region 14. Preferably, the fastening element and the landing zone may be disengaged to check the diaper for soiling without compromising the ability to use the fastener. Alternatively, other absorbent article fastening systems are also possible, including tapes, adhesives, safety pins, buttons, snaps, belts and cinching systems.

As stated previously, the invention has been described in connection with a diaper. The invention, however, is not intended to be limited to application only in diapers. Specifically, the absorbent cores of the preferred embodiments may be readily adapted for use in other absorbent garments besides diapers, including, but not limited to, training pants, feminine hygiene products and adult incontinence products.

The underlying structure beneath the top sheet 24 may include, depending on the diaper construction, various combinations of elements, but in each embodiment, it is contemplated that the absorbent garment will preferably include an absorbent core 28. For example, additional layers may be disposed between the top sheet 24 and absorbent core 28, and/or other additional layers may be disposed between these layers, or between absorbent core 28 and back sheet 26. The additional layer(s) may include a fluid transfer layer, a fluid handling layer, a storage layer, a wicking layer, a fluid distribution layer, and any other layer(s) known to those having ordinary skill in the art.

Although the absorbent core 28 depicted in FIG. 1 has a substantially rectangular cross-sectional and plan view shape, other shapes may be used, such as a "T" shape or an hourglass shape. The shape of the absorbent core 28 may be selected to provide the greatest absorbency with a reduced amount of material. The absorbent core may be associated with the top sheet 24, back sheet 26, or any other suitable part of the garment 10 by any method known in the art, in order to fix the absorbent core 28 in place. In addition to the respective layers in the absorbent core 28, as will be described in greater detail hereinafter, the overall absorbent core 28 may be enclosed within a tissue wrapping, as disclosed in U.S. Pat. No. 6,068,620, the disclosure of which is incorporated by reference herein in its entirety. Skilled artisans are capable of designing and wrapping a suitable absorbent core 28 of the invention, using the guidelines provided herein.

Any suitable absorbent material may be used for absorbent core 28. Absorbent cores containing a mixture of fibrous material and superabsorbent polymers (SAP) are well known in the art and described, for example, in U.S. Pat. Nos. 5,281,207, and 6,068,620 to Chmielewski, and U.S. Pat. No. 5,863,288, to Baker, the disclosures of each of which are herein incorporated by reference in their entirety and in a manner consistent with this disclosure. The fibrous material can be any fibrous material capable of absorbing fluids, or adsorbing and capable of retaining SAP particles within its matrix. Preferred fibrous materials may be selected from tow fibers, cellulose acetate fibers, rayon fibers, Courtauld's LYOCELL fibers, polyacrylonitrile fibers, surface-modified (hydrophilic) polyester fibers, surface-modified polyolefin/polyester bicomponent fibers, surface-modified polyester/polyester bicomponent fibers, cotton fibers, or blends thereof. In addition, rayon, Courtauld's LYOCELL, polyacrylonitrile, pulp fibers, cotton fibers and cotton linters are alternatively preferred. The remaining fibers, surface-modified polyolefin/polyester bicomponent fibers, and surface-modified polyester/polyester bicomponent fibers are also believed to be effective fibrous materials for use in the invention.

Any superabsorbent polymer (SAP) now known or later discovered may be used in absorbent core 28, so long as it is capable of absorbing liquids. Useful SAP materials are those that generally are water-insoluble but water-swellable polymeric substance capable of absorbing water in an amount that is at least ten times the weight of the substance in its dry form. In one type of SAP, the particles or fibers may be described chemically as having a back bone of natural or synthetic polymers with hydrophilic groups or polymers containing hydrophilic groups being chemically bonded to the back bone or in intimate admixture therewith. Included in this class of materials are such modified polymers as sodium neutralized cross-linked polyacrylates and polysaccharides including, for example, cellulose and starch and regenerated cellulose which are modified to be carboxylated, phosphonoalkylated, sulphoxylated or phosphorylated, causing the SAP to be highly hydrophilic. Such modified polymers may also be cross-linked to reduce their water-solubility.

The components described herein are assembled to form an absorbent garment. Adhesives are used in many embodiments to hold the components in the desired positions. Fixing the above described elastic components into position may provide a number of challenges as the adhesive must be distributed so that the gathers that form are smooth and properly placed while avoiding excess adhesive that may cause unwanted stiffness and increased production costs for example.

Figure 2:
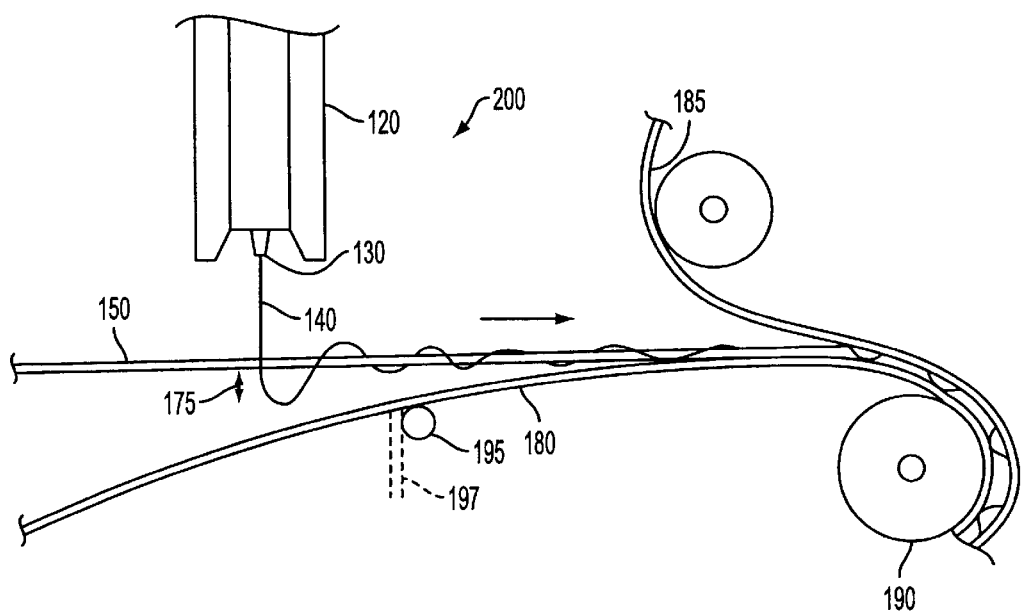
FIG. 2 is a partial side view of a system for applying fluid adhesive fibers to strands, and for bonding adhesive coated strands to substrates according to an exemplary embodiment of the invention.

Referring now to FIG. 2, an exemplary embodiment of a system 200 for applying fluid filaments including adhesives to strands, and in some embodiments, bonding adhesive coated strands onto substrates is shown. The exemplary system 200 dispenses hot melt adhesive fibers (fibers are also referred to herein as filament fluid fibers, fluid fibers, adhesive filaments or fluid filaments) 140 from one or more adhesive dispensing nozzles 120, which are preferably nozzles having one or more adhesive dispensing orifices 130. The present invention is applicable to applying an adhesive filament 140 to a strand 150, capturing substantially all of the adhesive onto the strand 150 and preventing unwanted applications of fluid onto an underlying substrate 180 or other area such as other materials of the garment or on the surface of manufacturing equipment, for example. In an exemplary embodiment, the adhesive is applied to stretchable elastic strands 150 that then may be attached to components of a variety of absorbent garments.

The methods of the present invention are particularly useful where it is desirable generally to precisely control the dispensing of relatively viscous fluids, including but not limited to hot melt adhesive fibers, onto a strand and in some applications thereafter to bond adhesive coated strands onto substrates. The adhesive fibers dispensed are not necessarily limited to hot melt fibers but are more generally any adhesive that may be controllably dispensed so that substantially the entire fluid is captured by the strand 150.

Referring to FIG. 2, the nozzle 120 dispenses an adhesive fiber 140 toward an isolated strand 150 drawn along a path so that at least a portion of the fluid fiber 140 crosses the path of the strand 150 and contacts the strand so that the fluid fiber 140 attaches thereto. The spatially isolated strand 150 captures substantially all of the adhesive fiber 140 dispensed from the nozzle 120, whereby the strand 150 is at least partially coated with fluid. By capturing substantially all of the fluid dispensed from the nozzle 120 onto the spatially isolated strand 150 there is little or no wasted fluid, thereby economizing the application thereof. Capturing substantially all of the fluid fiber 140 onto the strand 150 also reduces the likelihood that fluid will spill-over or be applied inadvertently to unintended areas, for example underlying substrates 180.

The fluid fiber 140 preferably is a substantially continuous fiber, although it may be intermittently discontinuous. For example it may be desirable in some embodiments to apply adhesive to a strand(s), preferably, elastic strands, along only a portion of their lengths, so that portions of the elastics do not receive an adhesive coating and do not adhere to the garment. In one embodiment of the invention this may be accomplished by intermittently cutting off the supply of adhesive to the orifice 130. In such an embodiment, a backflow device may be used in the nozzle or pump supplying adhesive to the nozzle, which draws adhesive out of the orifice and back into the nozzle. Such a back flow device may allow for relatively precise cutoffs. Other methods of momentarily ceasing the application of adhesive to strands may also be employed as will be evident to those of ordinary skill in the art in light of the teachings herein.

As FIG. 2 illustrates, the adhesive fiber 140 preferably is dispensed from a fixed orifice 130 positioned at a position above the strand 150 to be coated. The strand 150 is fed past the fixed orifice 130 in the machine direction in an orientation approximately normal to the direction of adhesive fiber 140 movement from the orifice 130. The viscosity and mass of adhesive fiber 140 dispensed. from the nozzle are selected or controlled so that the spatially isolated strand 150 captures substantially all of the adhesive fiber 140 dispensed from the nozzle 120 through the orifice 130. Variations in the dispensing of the adhesive fiber 140 from the nozzle 120, resulting for example from supply pressure changes and residue accumulation in the nozzle orifice and other factors, may result in adhesive fiber 140 discontinuities or in adhesive dispensing irregularities that occasionally prevent the adhesive fibers 140 or portions thereof from being captured entirely by the strand 150. In the case of hot melt adhesives the viscosity may in part be controlled by adjusting the temperature of the adhesive. Suitable hot melt adhesives may for example include:

AtoFindley H2420F (now known as Bostik Findley),

AtoFindley H2587-01,

National Starch & Chemical 34-5644,

National Starch & Chemical 34-578A,

HB Fuller HL-1486 UZP.

Generally the operating temperature range for these hot melt adhesives is 280°–350° F.

Figure 3:
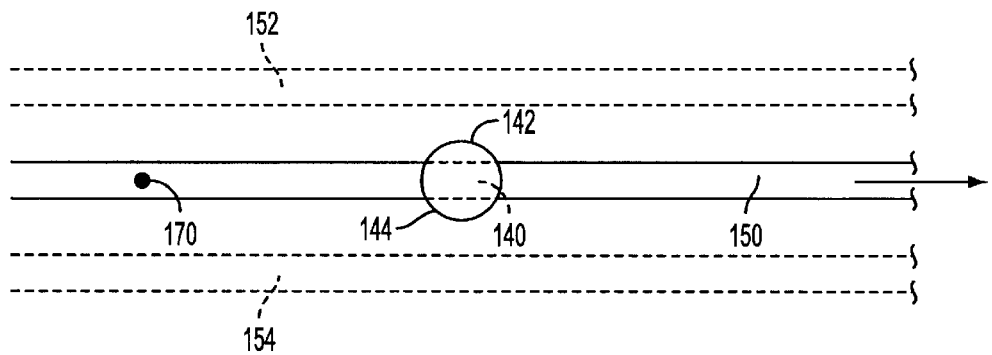
FIG. 3 is a schematic diagram showing the various positions of the strand with respect to the adhesive filament as viewed from above.
Figure 4:
FIG. 4 is a schematic diagram showing the path of point P on a strand as the strand moves generally forward in the machine direction.

As the strand 150 moves forward in the machine direction (e.g., in the direction of the arrow of FIG. 2) it also moves back and forth (e.g. oscillates) in the cross direction (e.g., orthogonal to the machine direction) and in a plane normal to the path of the adhesive fiber 140. As shown in FIG. 3, the strand 150 oscillates between positions 152 and 154 passing beyond opposing sides 142, 144 of adhesive filament 140 as it moves back and forth in the cross direction. The path of point P 170 as the strand 150 moves forward in the machine direction is shown in FIG. 4 as it would appear when viewed from above the strand 150. The strand 150 may be oscillated in the cross direction by any known mechanism capable of oscillating a strand, such as mechanical oscillation by oscillating the strand feed roller 1500 (FIG. 6), or belt for example, or other oscillating mechanisms 155 known to those skilled in the art.

The oscillating strand 150 captures substantially the entirety of the adhesive fiber 140 due to the loops that are created in the adhesive filament 140 as the strand 150 is moved beyond adhesive fiber 140 opposing sides 142 and 144. All sides of the strand 150 are at least partially coated with fluid fiber as the loops experience a "rope" effect and wrap onto the surface of the strand 150. Thus applied, the adhesive fibers 140 coat the strand 150 substantially uniformly along the axial dimension or length thereof. Uniform application of adhesive fibers 140 are desirable in the manufacture of absorbent garments where it is desirable to uniformly bond an adhesive coated elastic strand onto a fabric substrate to uniformly bunch the fabric forming waist bands and other stretchable portions thereof. Substantially uniformly applying the adhesive fibers 140 along the axial dimension of the strand 150 without coating the entire strand also substantially reduces adhesive usage while providing relatively uniform bonding to the substrate.

Figure 5:
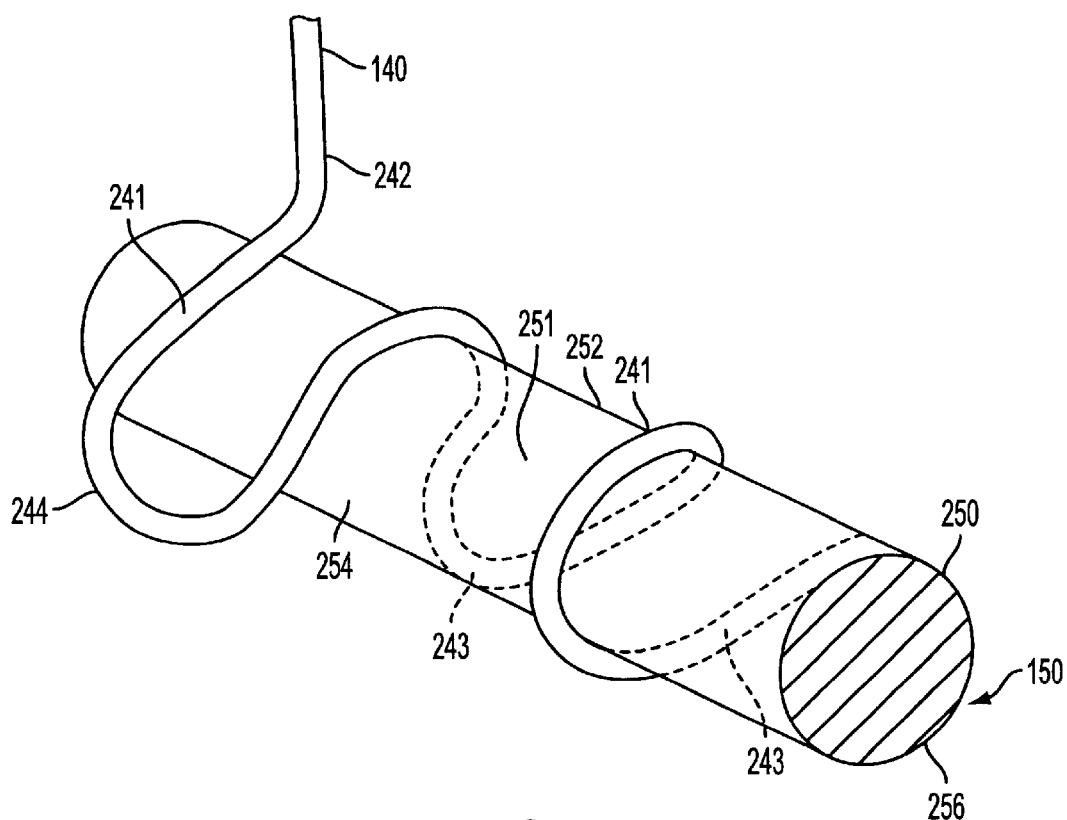
FIG. 5 is a partial perspective view of a strand at least partially coated with fluid adhesive on all sides thereof according to an exemplary embodiment of the invention.

FIG. 5 illustrates, more particularly, the fiber portions 242 and 244 draping downwardly along the corresponding sides 252 and 254 of the strand 150 after other fiber portions 241 contact the strand 150. The fiber portions 242 and 244 preferably are dispensed by the nozzle 120 to extend sufficiently outwardly beyond the corresponding sides 252 and 254 of the strand 150 so that portions 243 thereof adhere also to an underside 256 of the strand 150. In some applications, the fiber portions 242 and 244 may even extend and adhere down along one side of the strand, across the underside thereof, and back upwardly along the opposing side of the strand 150, sometimes wrapping more than once about the strand.

The portions 242 and 244 of the fiber 140 drape over the strand 150 under the influence of momentum or gravity or a combination thereof as the strand 150 moves back and forth across the path of the adhesive fiber 140, and ultimately the fiber 140 adheres at least partially to all sides of the strand 150 including a top side 251, opposing sides 252 and 254, and the underside 256 thereof. The adhesive fiber 140 is dispensed preferably from the nozzle 120 located above the isolated strand 150, and adheres initially to the top side 250 of the strand 150. The fiber 140 then migrates downwardly along the sides of the strand 150 and across the underside thereof to at least partially coat all sides thereof. The adhesive may thus be applied uniformly along the axial dimension of the strand 150, without coating the entire strand, thereby economizing on the application of adhesive and at the same time applying adequate amounts thereof to the strand 150 to ensure uniform bonding of the strand 150 along the axial dimension thereof to the substrate.

The fiber portions 242 and 244 preferably are not dispensed to extend so far outwardly beyond the corresponding sides 252 and 254 of the strand 150 that the fluid fiber 140 can not be captured substantially entirely by the strand 150. The fluid fiber mass flow rate, fluid viscosity, size and stability of the fluid fiber 140 are among the factors that limit the extent to which the fiber 140 may extend beyond the sides of the strand 150 and ultimately be substantially entirely captured thereby.

Precisely controlling the dispensing of fluid fibers from the nozzle 120 ensures that the strand 150 captures substantially all of the fluid fiber 140. Precisely controlling the dispensing of the fluid fibers 140 also ensures that fluid is applied at least partially to substantially all sides of the strand 150 and substantially uniformly along the axial dimension thereof. By appropriately controlling the dispensing of the fluid, and generally the rate at which the strand 150 is drawn relative to the nozzle 120 and the rate of side to side movement of strand 150, it is possibly to accurately control the amount or quantity of fluid fibers applied to the strand 150.

The elastic strands may have a circular or non-circular shape, such as an elliptical or rectilinear or other shape, that may have one or more long axis and one or more short axis. In such a case, it may be desirable to ensure that the aspect ratio (as measured by the long axis size divided by the short axis size) is not so great as to inhibit the ideal coating of the elastic. In an exemplary embodiment the aspect ratio is in the range of 1 to 2 with values at or near 1 preferred.

The speed at which the elastic strand is drawn past the adhesive nozzle may affect the adhesive coating process. If the strands are moving too fast, they may receive an insufficient amount of adhesive coating. If the strands are moving too slowly, they may receive too much adhesive. Further, the speed of the elastic strands should be matched to the viscosity and flow rate of the adhesive such that the adhesive filaments droop around the strands partially coating the various surfaces of the strand. For hot melt adhesives the viscosity of the adhesive may generally be varied by heating or cooling the adhesive.

In applications where the strand 150 is bonded between substrates 180, 185 (FIGS. 2 and 6) and where the strand 150 has a tendency to twist prior to bonding onto a single substrate, it is desirable to at least partially coat all sides of the strand 150 with adhesive, to ensure complete bonding of the strand 150 to the substrate 180. It is desirable in other applications, for example where an elastic strand 150 forms a waist band or other stretchable portion of a garment, to apply adhesive substantially uniformly along the axial dimension thereof, and preferably at least partially to all sides of the strand, to ensure uniform bonding of the strand 150 along an axial dimension thereof to a fabric substrate, thereby providing substantially uniform bunching of the fabric as the elastic strand contracts. The extent to which the strand 150 is coated with adhesive is controlled generally by the adhesive fiber mass flow rate, strand 150 oscillation amplitude and frequency, and the strand 150 drawing rate (e.g. speed of movement in the machine direction).

Figure 6:
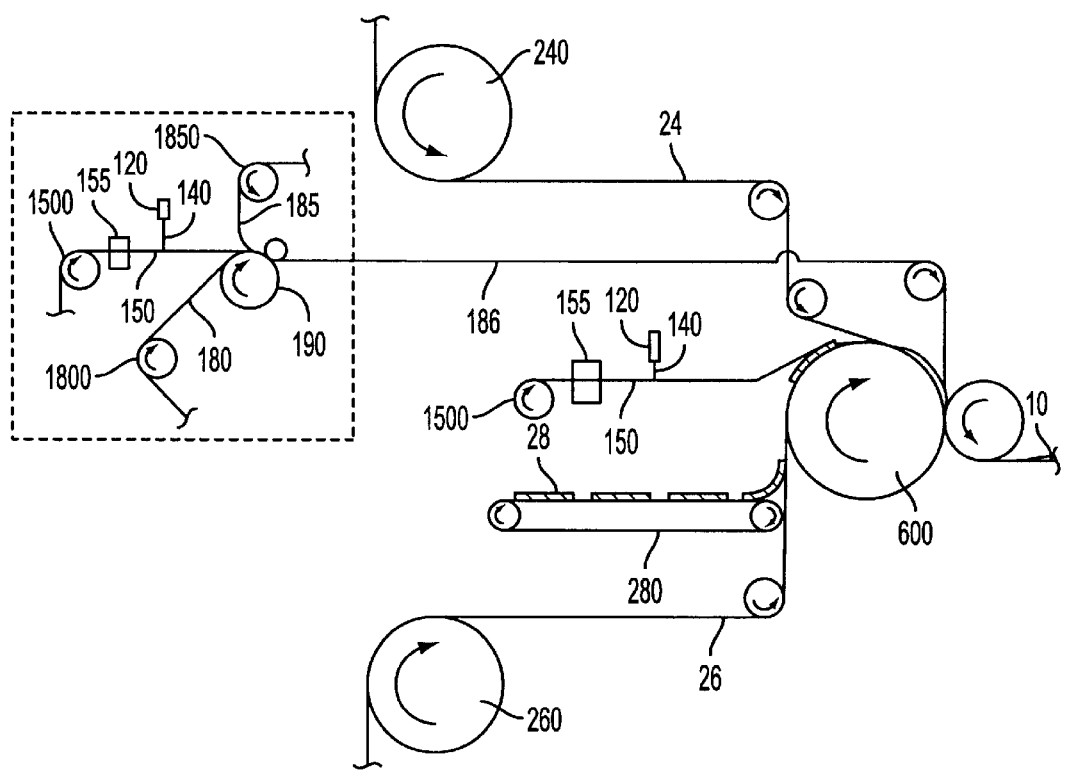
FIG. 6 is a schematic of an apparatus for making an absorbent garment according to an exemplary embodiment of the invention.

Referring now to FIGS. 2 and 6, FIG. 2 and the dotted outlined portion of FIG. 6 illustrate the application of adhesive fibers 140 onto a strand 150 and the bonding of the adhesive coated strand 150 to a substrate 180, and then forming a laminate 186 comprising a first substrate 180, a second substrate 185, and an adhesive coated strand 150 disposed there between. Initially, the strand 150 is supplied along a path separated spatially from the substrate 180 by strand feed roller 1500. The adhesive fiber 140 is dispensed toward the isolated strand 150 so that at least a portion of the adhesive fiber 140 crosses the path of the strand 150 as the strand moves forward in the machine direction (direction of arrow in FIG. 2), and as the strand moves side to side in the cross direction past the nozzle 120. As discussed above, the strand 150 preferably oscillates back and forth across the path of the adhesive fiber 140, beyond opposing sides thereof. The strand 150 captures substantially all of the adhesive fiber 140 when the strand 150 is spatially separated from the substrate 180 to at least partially coat the strand 150 with adhesive. Preferably, the adhesive is applied at least partially to all sides of the strand 150 to ensure uniform bonding of the strand along an axial dimension thereof to the substrate 180. The adhesive coated strand 150 then is contacted with the substrate 180 to bond the strand 150 thereto before the adhesive sets.

In the manufacture of absorbent garments, the substrate 180 preferably is a fabric, such as top sheet material 24, or back sheet material 26, as discussed above, and the strand 150 is an elastic strand that is stretched by applying tension thereto before bonding to the substrate 180. As illustrated in FIGS. 2 and 6 the strand 150 and the substrate 180 are both drawn by common roller 190. In this exemplary application, the stretched adhesive coated elastic strand 150 is also bonded to a second substrate 185, which also may be drawn by the roller 190, whereby the strand 150 is disposed between and bonded to the substrate 180 and the substrate 185 thus forming a laminate 186. The adhesive is applied at least partially to all sides of the strand 150 and preferably substantially uniformly along the axial dimension thereof as discussed above to ensure that the strand 150 bonds uniformly to both first and second substrates 180,185. As one of ordinary skill in the art will appreciate FIG. 2 shows an exemplary assembly arrangement, and that other configurations may be employed without undue experimentation.

In applications where the substrate 180 is adjacent the strand 150 and opposite the adhesive dispensing nozzle 120, it is preferred to spatially separate the substrate 180 from the strand 150 by a distance greater than a droop distance 175 of the adhesive fiber 140 below the strand 150 opposite the adhesive nozzle 120 to prevent adhesive from inadvertently adhering to the substrate 180. In other applications, the adhesive 140 may be applied to the strand 150 away from the substrate 180, to ensure that no adhesive 140 is inadvertently applied thereto. For example, the substrate 180 may be supplied from below roller 195 along the path 197 away from fluid fibers 140 dispensed from the nozzle 120.

The nozzle 120 in some embodiments may have a plurality of orifices 130 dispensing a plurality of at least two adhesive fibers 140 from a corresponding plurality of adhesive orifices toward a corresponding plurality of isolated strands 150, wherein each of the plurality of isolated strands 150 is oscillated back and forth across the path of the corresponding adhesive fiber 140. Alternatively a plurality of fibers 140 may be applied to a single isolated strand 150 as the strand 150 is oscillated back and forth across the path of corresponding adhesive fibers 140.

Each strand 150 captures substantially all of the adhesive fiber 140 dispensed from the corresponding adhesive orifice when the strand 150 is spatially separated from the substrate to at least partially coat the strand 150 with adhesive. The strands are preferably oscillated back and forth across the path of the corresponding adhesive fiber beyond opposing sides thereof to at least partially coat all sides of each strand with adhesive, preferably substantially uniformly along the axial dimension thereof. In some applications, the plurality of adhesive coated strands are subsequently contacted with one or more substrates to bond the plurality of strands to the one or more substrates as discussed above.

FIG. 6 illustrates a schematic of a preferred apparatus for making a laminate in accordance with the invention, and for making an absorbent garment in accordance with the invention. The portion of FIG. 6 separated by the dotted lines relates to an optional apparatus for forming a laminate 186, and correlates generally to the apparatus of FIG. 2. As will be described later, laminate 186 may optionally be included in absorbent garment 10 either before (not shown) or after forming station 600 where the top sheet material 24, back sheet material 26, and absorbent core 28 are brought into contact with one another to form the absorbent garment 10.

Strand 150 is coated with a filament of fiber 140 in accordance with the procedures outlined above. Specifically, strand 150 is supplied by strand supply mechanism 1500 in a machine direction (from the left to the right in FIG. 6). Strand 150 travels in the machine direction underneath a substantially continuous fluid filament 140, preferably an adhesive filament fiber 140, that is dispensed from nozzle 120. Strand 150 is oscillated in a cross-machine direction by an oscillating mechanism 155 in such a manner that adhesive filament fiber 140 substantially coats strand 150, as described above.

Laminate 186 can be formed simply by disposing adhesive-coated strand 150 between a first substrate 180 and a second substrate 185, which are supplied via first and second substrate supply mechanisms 1800, 1850, respectively. The respective components then are drawn into roller 190 to form laminate 186. Any first and second supply mechanism 1800, 1850, as well as strand supply mechanism 1500 can be used in the invention so long as they are capable of supplying a continuous supply of material. Preferably, the respective supply mechanisms are comprised of feed rollers, conveyors, belts, and the like.

FIG. 6 illustrates forming the laminate 186, and then feeding the laminate to the forming station 600 to form absorbent garment 10. Laminate 186 can be fed prior to disposing the absorbent core 28 between top sheet material 24 and back sheet material 26, or afterwards. Laminate 186 preferably includes two outer non-woven sheets, (e.g., first and second substrates 180, 185), having disposed there between an elastic material. Laminate 186 may be elongated prior to forming part of absorbent garment 10, or it may be attached thereto in a relaxed condition. Laminate 186 may form part of or all of the one or more laterally disposed tabs 34 of garment 10 (FIG. 1), thereby rendering the tabs 34 elastic, or laminate 186 may be used in the first or second waist region 12, 14 to form tummy elastics, and the like. In one embodiment of the invention, laminate 186 is not included in the absorbent garment 10, and hence, it is an optional component thereof and indicated by the dashed outline in FIG. 6.

Absorbent garment 10 of the invention can be formed using any conventional forming apparatus used to form an absorbent garment, so long as the strand(s) 150 disposed therein are coated with the fluid filament 140 in accordance with the procedures described above. FIG. 6 depicts an embodiment of a manufacturing process for producing a garment 10 having the desired features of the present invention. The various parts of the garment are described in more detail elsewhere herein.

In the preferred embodiment depicted in FIG. 6, a continuous supply of back sheet material 26 is provided along the machine direction to forming station 600 via back sheet supply roller 260. Absorbent cores 28 preferably are supplied via absorbent core supply mechanism 280, and then deposited on the back sheet material 26 (or another layer or layer(s) interposed there between) on the surface that will eventually become the inner surface of the back sheet 26 of the garment 10. The absorbent cores 28 may be bonded or otherwise operatively associated with the back sheet material 26 at this point or thereafter. Skilled artisans also will recognize that absorbent cores 28 need not be bonded or operatively associated with back sheet material 26, or top sheet material 24, and that other layers may be present between back sheet 26 and absorbent core 28.

A continuous supply of top sheet material 24 is provided substantially in the machine direction to forming station 600 via top sheet supply roller 240. The supply of top sheet material 24 preferably overlays the back sheet material 26 and encases the absorbent cores 28. The top sheet material 24 may be adhesively bonded to, or otherwise operatively associated with, the back sheet material 26 or other parts of the assembly at this location or hereafter. The method also includes providing to forming station 600, at least a continuous supply of strand 150, preferably an adhesively-coated elastic strand 150 that may serve as leg gather elastic elements 30 in the final garment (FIG. 1).

The adhesively-coated elastic strand(s) 150 is provided to forming station 600 via strand supply mechanism 1500.

Prior to providing elastic strand(s) 150 to forming station 600, however, the strand(s) is coated with an adhesive 140 in the manner discussed above. That is, strand 150 is oscillated in the cross machine direction by oscillating mechanism 155, while strand 150 passes underneath a continuous filament of adhesive 140 supplied from nozzle 120, thereby forming adhesively-coated elastic strand(s) 150. It is preferred that the adhesively-coated elastic stand(s) 150 is stretched or extended while providing it to forming station 600. Preferably, it is extended to between approximately 5% and approximately 500% of its relaxed length and more preferably extended to between approximately 200% and 400% of its relaxed length. The adhesively-coated elastic strand(s) 150 then may be adhered to an element of the garment 10, e.g., to the top sheet material 24 or back sheet material 26, but preferably not adhered to other elements of the garment, e.g., not adhered to absorbent core 28.

Any strand supply mechanism 1500 can be used to supply strand(s) 150 to forming station 600. Suitable supply mechanisms are disclosed in, for example, U.S. Pat. Nos. 5,147,487, 5,188,627, 5,745,922, 6,098,203, and RE 37,154E, the disclosures and drawings of which are incorporated by reference herein in their entirety, and in a manner consistent with this disclosure. Any of the methods for supplying elastic elements to a forming station disclosed therein are suitable in the present invention.

The respective component parts of the absorbent garment 10 are brought together and associated with one another at forming station 600. Here, any adhesive or other joining mechanism applied to back sheet material 24, top sheet material 26, or strand(s) 150 will serve to adhere the respective materials to one another. In addition, other components may be included in the garment at this stage or later, and other processing steps may take place to form garment 10. For example, an additional ultrasonic bonding apparatus may be employed, additional adhesive applicators may be disposed to apply adhesive to top sheet 24, back sheet 26, strand(s) 150, absorbent core 28, and the like.

After bringing the components together at forming station 600, the absorbent garment preferably is further processed by cutting and folding, and/or carrying out other processing procedures (e.g., providing standing leg gathers 40, etc.). For example, the top sheet material 24 and back sheet material 26 preferably are cut to form leg-hole cutouts on each side of the assembly. Any suitable cutting device may be used, such as fixed blades, cutting drums or reciprocating cutters. The top sheet material 24 and back sheet material 26, and any other components may also be operatively associated with one another during the same operation. For example, a single device may provide blades to cut the leg hole cutouts, and also provide anvils to form ultrasonic bonds or heated elements to activate adhesives previously deposited on one or more of the parts. Additional heating drums or pressure devices may be employed to provide suitable seals along the respective front, rear, left, and right side and arcuate edges of garment 10, and then the garment cut and severed from the moving web.

Additional processing steps also may take place to fasten the front and rear waist edges 12, 14 to one another. For example, the garment 10 may be folded in half, and then adhesives, ultrasonic welds, and the like used to join the respective front and rear side edges 18 to one another, thereby forming a disposable pants type garment 10. Alternatively, tabs (34 in FIG. 1) may be attached to or integrally formed with, top sheet material 24 or back sheet material 26 at the left and right rear side edges 18, whereby the tabs support fastening elements. As mentioned above, the tabs 34 may be formed from laminate 186, prepared as described above. Any fastening elements may be used, including, inter alia, hooks, loops, tapes, clips, snaps, and the like. At least one target device 38 then can be disposed at or near the front waist region 14 of the garment 10 whereby the at least one target devices forms a landing zone and otherwise cooperates or associates with the fastening elements. Suitable target devices include, hooks, loops, tape landing zones, clips, snaps, etc. Those skilled in the art are capable of associating the front waist region 14 with the rear waist region 12 to form a pants-type absorbent garment 10, using the guidelines provided herein.

One skilled in the art will understand that the locations of the various parts of the invention during the assembly process, and the intervals at which parts are placed on the assembly, are selected such that the various parts are in their proper location in the final products. In addition, other parts, such as waist elastic elements 32 or standing leg gathers 40, may be incorporated into the assembly during the assembly process, and other processes, such as folding and packaging, may be incorporated into the assembly process. Also, it should be understood that any suitable method may be used to introduce the various parts to the assembly line, such as rollers, vacuum drums, or reciprocating stamps. Finally, it should also be understood that the order of the various forming procedures may be modified, combined, or rearranged to provide for various assembly sequences that will provide substantially the same finished product, and all such variations are within the scope and spirit of the present invention and are within the knowledge and skill of those skilled in the art in light of the present teachings. For example, application of top sheet material 24 may take place subsequent to, or just prior to forming station 600. Other modifications will be apparent to those skilled in the art.

The invention has been described in connection with the preferred embodiments, these embodiments, however, are merely for example and the invention is not restricted thereto. It will be understood by those skilled in the art that other variations and modifications can easily be made within the scope of the invention as defined by the appended claims.

What is claimed is:

1. A method for applying a fiberized fluid adhesive to a strand, the method comprising:

supplying a strand along a machine direction;

dispensing a substantially continuous fluid adhesive fiber toward the strand in a direction normal to the machine direction;

oscillating the strand back and forth in a direction orthogonal to the machine direction and in a plane substantially normal to the continuous fluid adhesive fiber across the path of the fluid adhesive fiber as the fluid adhesive fiber is dispensed toward the strand;

capturing substantially all of the continuous fluid adhesive fiber on the strand; and coating all sides of the strand at least partially with the fluid adhesive fiber.

2. The method of claim 1, oscillating the strand beyond the path of the fluid adhesive fiber as the fluid adhesive fiber is dispensed toward the strand, thereby forming loop portions of fluid adhesive fiber and wrapping the loop portions of fluid adhesive fiber about the strand.

3. The method of claim 1, the strand is an elastic strand.

4. The method of claim 1, the fluid adhesive fiber is a hot melt adhesive.

5. The method of claim 1, wherein the dispensing of the substantially continuous fluid adhesive fiber is initiated and terminated at predetermined intervals.

6. The method of claim 1, the method further comprising:
supplying the strand along a path separated spatially from a first substrate;
dispensing the fluid adhesive fiber from above the strand;
capturing substantially all of the fluid adhesive fiber on the strand when the strand is spatially separated from the first substrate;
coating all sides of the strand at least partially with the fluid adhesive fiber when the strand is spatially separated from the first substrate; and
contacting the adhesive coated strand with the substrate to bond the strand to the first substrate.

7. The method of claim 6, wherein the strand is an elastic strand, the substrate is a fabric for an absorbent garment, and the method further comprises stretching the elastic strand before bonding the elastic strand to the substrate.

8. The method of claim 6, further comprising spatially separating the strand from the first substrate by a distance greater than a droop distance of the fluid adhesive fiber below the strand where the fluid adhesive fiber is dispensed to the strand.

9. The method of claim 6, the adhesive fiber is a hot melt adhesive.

10. The method of claim 6, further comprising bonding the adhesive coated strand to a second substrate, whereby the strand is disposed between the first substrate and the second substrate.

11. The method of claim 10, wherein the strand disposed between the first and second substrates forms a laminate.

12. The method of claim 10, wherein the strand is an elastic strand, and the substrate is a fabric for an absorbent garment.

13. The method of claim 6, further comprising:
supplying a plurality of strands separated spatially from the substrate and each other in a machine direction;
dispensing a plurality of fluid adhesive fibers from a corresponding plurality of adhesive orifices toward a corresponding one of the plurality of strands in a direction substantially normal to the machine direction;
oscillating each of the plurality of strands back and forth in a direction orthogonal to the machine direction and in a plane substantially normal to the fluid adhesive fiber across the path of the corresponding adhesive fibers, as the fluid adhesive fibers are dispensed toward the strands;
capturing substantially all of each adhesive fiber on the corresponding strand when the strand is substantially separated from the substrate;
at least partially coating all sides of each strand with the corresponding adhesive fiber when the strand is spatially separated from the substrate; and
contacting the plurality of adhesive coated strands with the substrate to bond the plurality of strands to the substrate.

14. A method for applying adhesive to a strand for bonding the strand to a substrate in the production of an absorbent garment, the method comprising:
supplying a strand along a path separated spatially from the substrate in a machine direction;
dispensing a substantially continuous fluid adhesive fiber toward the strand in a direction normal to the machine direction;
oscillating the strand back and forth in a direction orthogonal to the machine direction and in a plane substantially normal to the continuous fluid adhesive fiber across the path of the adhesive fiber as the adhesive fiber is dispensed toward the strand;
capturing substantially all of the continuous fluid adhesive fiber on the strand when the strand is spatially separated from the substrate; and
contacting the adhesive coated strand with the substrate to bond the adhesive-coated strand to the substrate.

15. The method of claim 14, oscillating the strand beyond the path of the fluid adhesive fiber as the fluid adhesive fiber is dispensed toward the strand, thereby forming loops of fluid adhesive fiber and wrapping the loop portions of the fluid adhesive fibers around the strand.

16. The method of claim 14, wherein the strand is an elastic strand, the substrate is a fabric for an absorbent garment, and the method further comprises stretching the elastic strand before the elastic strand is bonded to the substrate.

17. The method of claim 14, further comprising dispensing the fluid adhesive fiber from above the strand, and spatially separating the strand from the substrate by a distance greater than a droop distance of the fluid adhesive fiber below the strand where the fluid adhesive fiber is dispensed to the strand.

18. The method of claim 14, the fluid adhesive fiber is a hot melt adhesive.

19. The method of claim 14, further comprising:
supplying a plurality of at least two strands along corresponding paths separated spatially from the substrate in a machine direction;
dispensing a plurality of substantially continuous fluid adhesive fibers from a corresponding plurality of adhesive orifices directed toward a corresponding one of the plurality of strands in a direction substantially normal to the machine direction;
oscillating each of the plurality of strands back and forth in a direction orthogonal to the machine direction and in a plane substantially normal to the fluid adhesive fibers across the path of the corresponding fluid adhesive fibers as the fluid adhesive fibers are dispensed toward the strands;
capturing substantially all of each corresponding adhesive fiber on the corresponding strand when the strand is spatially separated from the substrate; and
contacting the plurality of adhesive coated strands with the substrate to bond the plurality of strands to the substrate.

20. The method of claim 19, the plurality of strands are elastic strands.

21. The method of claim 19, the fluid adhesive fibers are a hot melt adhesive.

22. An apparatus for applying fluid filaments to a strand, the apparatus comprising:
a dispensing nozzle for dispensing fluid filaments to a strand;
a strand supplying mechanism for supplying a strand in a machine direction that is substantially normal to the path of the fluid filament dispensed from the dispensing nozzle; and
a mechanism for oscillating the strand in a direction orthogonal to the machine direction and in a plane substantially normal to the path of the fluid filament.

23. The apparatus of claim 22, wherein the strand is an elastic strand.

24. The apparatus of claim 22, wherein the fluid filament is a fluid adhesive filament.

25. The apparatus of claim 24, wherein the fluid adhesive filament is a hot melt adhesive.

26. The apparatus of claim 22, further comprising a mechanism initiating and terminating dispensing fluid filaments at predetermined intervals.

27. The apparatus of claim 22, the dispensing nozzles having a plurality of orifices for dispensing a plurality of adhesive fibers and the strand supply mechanism having a mechanism for supplying a plurality of strands separated spatially from each other.

28. A method of making an absorbent garment comprising:
providing a top sheet material, a back sheet material and an absorbent core;
applying a fluid filament to a strand including
supplying a strand along a machine direction;
dispensing a substantially continuous fluid filament toward the strand in a direction substantially normal to the machine direction;
oscillating the strand back and forth in a direction orthogonal to the machine direction and in a plane substantially normal to the continuous fluid filament fiber across the path of the fluid filament as the fluid filament is dispensed toward the strand;
capturing substantially all of the continuous fluid filament on the strand; and
coating all sides of the strand at least partially with the fluid filament; and
disposing the fluid filament-coated strand and the absorbent core between the top sheet material and the back sheet material.

29. The method of making an absorbent garment of claim 28, wherein the strand is an elastic strand.

30. The method of making an absorbent garment of claim 28, wherein the fluid filament is a fluid adhesive filament.

31. The method of making an absorbent garment of claim 30, wherein the fluid adhesive filament is a hot melt adhesive.

32. The method of making an absorbent garment of claim 28, wherein the dispensing of the substantially continuous fluid filament is initiated and terminated at predetermined intervals.

33. The method of making an absorbent garment of claim 28, further comprising:
supplying a plurality of strands separated spatially from the top sheet, back sheet, absorbent core and each other in a machine direction;
dispensing a plurality of fluid filaments from a corresponding plurality of fluid filament orifices toward a corresponding one of the plurality of strands in a direction substantially normal to the machine direction;
oscillating each of the plurality of strands back and forth in a direction orthogonal to the machine direction and in a plane substantially normal to the fluid filament across the path of the corresponding fluid filament as the fluid fibers are dispensed toward the strands;
capturing substantially all of each fluid filament on the corresponding strand when the strand is spatially separated from the substrate;
at least partially coating all sides of each strand with the corresponding fluid filament when the strand is spatially separated from the top sheet, back sheet and absorbent core; and
contacting the plurality of fluid filament coated strands with at least one of the top sheet and back sheet to bond the plurality of strands therewith.

34. A method of making an absorbent garment comprising:
providing a top sheet material, back sheet material, and an absorbent core wherein the absorbent core is disposed between the top sheet material and the back sheet material to form an absorbent assembly;
constructing a laminate including a first substrate, a second substrate and a strand disposed between the first and second substrates wherein the strand is supplied in a machine direction along a path separated spatially from the first and second substrates, a fluid fiber is dispensed toward the strand in a direction normal to the machine direction, the strand is oscillated back and forth in a direction orthogonal to the machine direction and in a plane substantially normal to the fluid fiber across the path of the fluid fiber as the fluid fiber is dispensed toward the strand, capturing substantially all of the fluid fiber on the strand, and coating all sides of the strand at least partially with the fluid fiber and the fluid fiber-coated strand is disposed between the first substrate and the second substrate; and
attaching the laminate to the absorbent core assembly.

35. The method of making an absorbent garment of claim 34, wherein the strand is an elastic strand.

36. The method of making an absorbent garment of claim 34, wherein the fluid filament is a fluid adhesive filament.

37. The method of making an absorbent garment of claim 36, wherein the fluid filament is a hot melt adhesive.

38. The method of making an absorbent garment of claim 34, disposing a plurality of fluid fiber-coated strands between the first and second substrate.

39. An apparatus for forming an absorbent garment comprising:
a top sheet supply mechanism for supplying a top sheet;
a back sheet supply mechanism for supplying a back sheet;
an absorbent core supply mechanism for supplying an absorbent core;
a forming station which receives the top sheet from the top sheet supply mechanism, the back sheet from the back sheet supply mechanism and the absorbent core from the absorbent core supply mechanism;
an apparatus for applying a fluid filament to a strand including,
a dispensing nozzle for dispensing a fluid filament to a strand,
a strand supply mechanism for supplying a strand in a machine direction that is substantially normal to the path of the fluid filament dispensed from the dispensing nozzle, and
a mechanism for oscillating the strand in a direction normal to the machine direction in a plane substantially normal to the path of the fluid filament and coating at least a portion of the strand with the fluid filament; and
a forming station portion for disposing the absorbent core and fluid filament-coated strand between the top sheet and back sheet material forming an absorbent assembly.

40. The apparatus for forming an absorbent garment 39, wherein the strand is an elastic strand.

41. The apparatus of claim 39, wherein the fluid filament is a fluid adhesive filament.

42. The apparatus of claim 41, wherein the fluid adhesive filament is a hot melt adhesive.

43. The apparatus for forming an absorbent garment of claim 39, the forming station portion disposing a plurality of fluid filament strands between the top sheet and back sheet material.

44. The apparatus for forming an absorbent garment of claim 39 further comprising:
 a laminate formation station wherein the laminate formation station includes a first substrate supply mechanism for supplying a first substrate;
 a second substrate supply supply mechanism for supplying a second substrate;
 a laminate strand supply mechanism for a supply a laminate strand and
 an apparatus for applying a fluid filament to a laminate strand including:
  a dispensing nozzle for dispensing a laminate fluid filament to a laminate strand,
  a laminate strand supply mechanism for supplying filament to a laminate strand,
  a laminate strand in a machine direction that is substantially normal to the path of the laminate fluid filament dispensed from the dispending nozzle,
  an mechanism for oscillating the laminate strand in a direction orthogonal to the machine direction in a plane substantially orthogonal to the path of the laminate fluid filament and coating at least a portion of the laminate strand with the laminate fluid filament; and
 a laminate forming portion for disposing the laminate strand between the first substrate and the second substrate and forming a laminate,
 a laminate attachment station for attaching the laminate to the absorbent assembly.

45. The apparatus for forming an absorbent garment of claim 44, wherein the laminate strand is spatially separated from the first substrate and second substrate when the laminate fluid filament is dispensed to the laminate strand.

46. The apparatus for forming an absorbent garment of claim 44, wherein the laminate strand is an elastic strand.

47. The apparatus for forming an absorbent garment 44, wherein the laminate filament is a fluid adhesive filament.

48. The apparatus for forming an absorbent garment of claim 47, wherein the fluid adhesive filament is a hot melt adhesive.

49. The apparatus for forming an absorbent garment of claim 44, disposing a plurality of fluid filament-coated laminate strands between the first and the second substrates.

* * * * *